(12) United States Patent
Proksa

(10) Patent No.: US 6,561,695 B2
(45) Date of Patent: May 13, 2003

(54) CALIBRATION TABLE FOR A CONE-BEAM CT-APPARATUS

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/144,829

(22) Filed: Oct. 25, 2001

(65) Prior Publication Data

US 2002/0186819 A1 Dec. 12, 2002

(30) Foreign Application Priority Data

Oct. 25, 2000 (EP) .............................................. 00203697

(51) Int. Cl.[7] ................................................ A61B 6/00
(52) U.S. Cl. ........................ 378/207; 378/20; 378/163; 378/209
(58) Field of Search ................................ 378/4, 15, 20, 378/205, 207, 208, 209, 162, 163, 164; 5/601

(56) References Cited

U.S. PATENT DOCUMENTS

| | | | | |
|---|---|---|---|---|
| 3,581,088 A | * | 5/1971 | Engels | 378/209 |
| 4,233,507 A | | 11/1980 | Volz | 378/207 |
| 5,239,569 A | * | 8/1993 | Saleh et al. | 378/163 |
| 5,537,454 A | * | 7/1996 | Korver, II | 378/65 |
| 6,396,903 B1 | * | 5/2002 | Wenstrup | 378/164 |
| 6,460,206 B1 | * | 10/2002 | Blasche et al. | 378/209 |

\* cited by examiner

Primary Examiner—Drew A. Dunn
(74) Attorney, Agent, or Firm—John Vodopia

(57) ABSTRACT

The reconstruction in Cone-beam CT scanner requires a high accuracy of the tabletop (1) position determination. In sequential as well as in helical acquisitions projection data (20) from different tabletop (1) positions are combined. Additional position markers, manufactured as insertions (10) of a contrast material relative to the material of the tabletop (1), are introduced into the tabletop (1). These insertions (10) allow the determination of the true position of the tabletop (1) from projection data. This information can be used to either control the scanner mechanics or as a correction information for the reconstruction process.

7 Claims, 4 Drawing Sheets

CALIBRATION TABLE FOR A CONE-BEAM CT-APPARATUS

BACKGROUND OF THE INVENTION

Figures 1A, 1B, 1C:
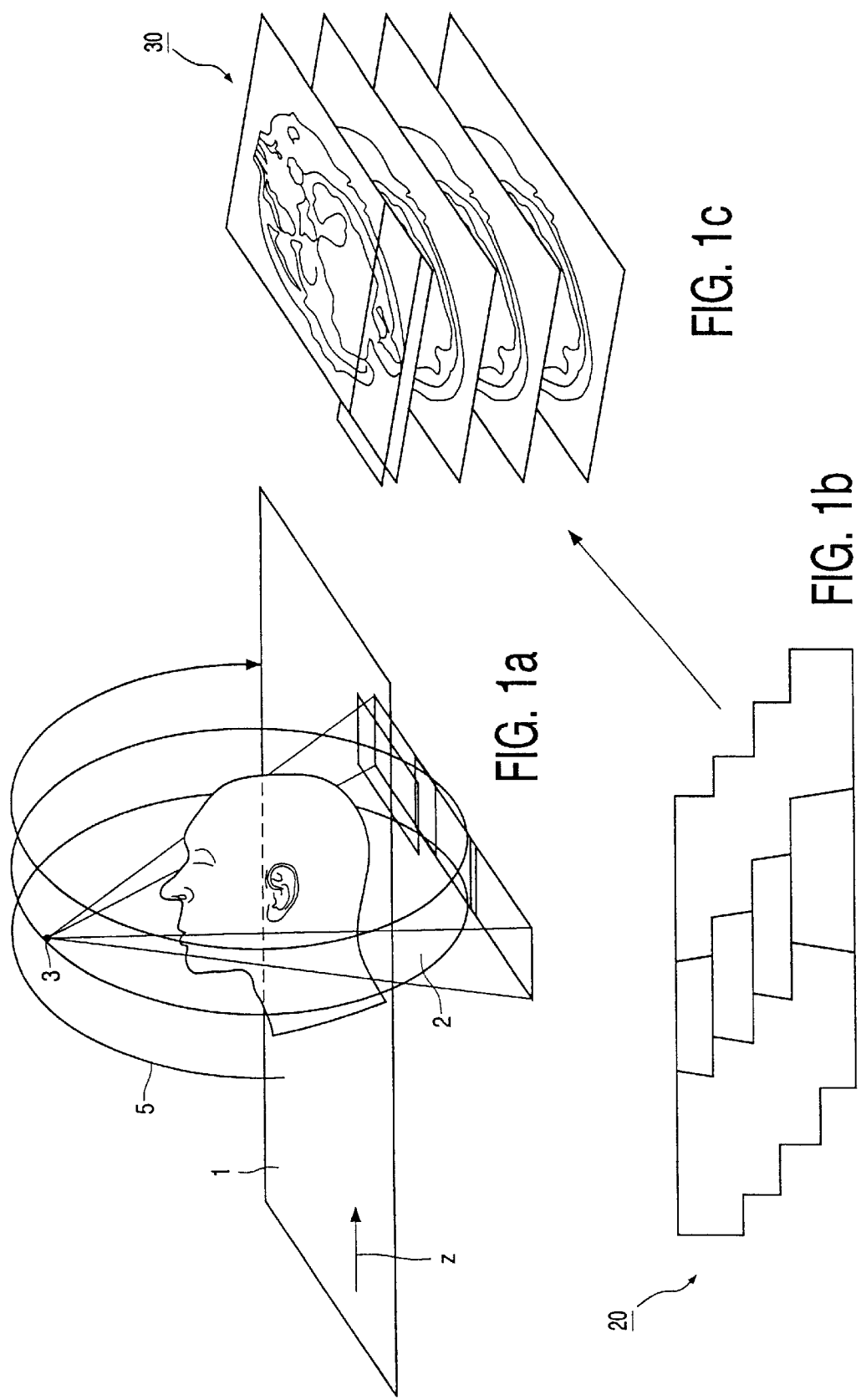

The present invention relates to the field of X-ray technology, namely to a CT-apparatus comprising an investigation bore with an X-ray source and an X-ray detector to generate an X-ray transmission image of an object to be investigated, a table with an elongated tabletop with a first longitudinal direction to support the object, which tabletop is translatable into the investigation bore in its first longitudinal direction, which tabletop comprises elongated mutually parallel insertions of a contrast material relative to the material of the tabletop for calibration purposes, said contrast material having a different X-ray attenuation coefficient than the material of the tabletop, said insertions having a second longitudinal direction.

A CT-apparatus of this type is known from U.S. Pat. No. 4,233,507. The CT-apparatus is generally used to perform an investigation of internal organs of a human body, based on the acquired X-ray transmission images from different directions. The human body comprises different tissues, which can be distinguished from each other due to the fact that such tissues have different radiation attenuation coefficients and, thus, have different characteristic X-ray absorption properties. It is important to precisely calibrate the CT-apparatus in order to be able to distinguish between tissues having similar radiation attenuation coefficients. In the known CT-apparatus an investigation table comprises calibration means to calibrate the Hounsfield's numbers in order to perform a correct calculation of corresponding radiation attenuation coefficients. For that purpose a number of elongated insertions is provided in the tabletop, every insertion having a known X-ray attenuation coefficient, characteristic to a specific tissue. The diagnostic data acquired by a CT-apparatus is often used for further patient treatment, for example for radiotherapy. It is important, therefore to correctly assign the acquired X-ray transmission information to the topology of the patient. This problem is of specific importance when one uses a cone-beam CT acquisition mode. In this mode it is possible to produce X-ray transmission images in sequential (step and shoot) or in helical acquisition, while the tabletop is continuously translated during the X-ray exposure.

SUMMARY OF THE INVENTION

It is an object of the present invention to provide a CT apparatus where the accuracy of the tabletop position determination is improved. The CT-apparatus according to the invention is characterized in that the insertions are arranged with the second longitudinal direction orthogonally to the first longitudinal direction, wherein the spacing between the insertions in the first longitudinal direction is smaller than a dimension of the X-ray detector in the first longitudinal direction. The present invention is based on the insight that the tabletop position is defined within the system of the CT-apparatus, for example by a read-out of corresponding potentiometers with a certain tolerance, which is usually in the order of 2 mm. To improve this tolerance one can consider the read-out of the potentiometers as a coarse calibration of the tabletop position and the usage of insertions as a fine tuning of the tabletop position. Such insertions will have an a-priori known dimensions and spacing between them in the first longitudinal direction. In a cone-beam CT-apparatus one uses a two-dimensional X-ray detector, which comprises an array of detector elements. Thus, for this acquisition mode the maximum spatial resolution (i.e. the minimum spatial uncertainty) in the first longitudinal direction will be equal to the size of the detector element in this direction. After the data are acquired the back-projection is performed to reconstruct the transmission images. This image reconstruction uses the signals from the whole array of detector elements in the first longitudinal direction, due to the fact that the X-ray detector has a finite size in the first longitudinal direction and the acquisition is performed with a cone beam. After the reconstruction is performed a tabletop coordinate is prescribed to each resulting image. In order to improve the determination of the tabletop position the insertions are used. Therefore, the spacing between the insertions in the first longitudinal direction must be smaller than the detector size in this direction. The absolute values for the size and the spacing of the insertions are determined by the compromise between a substantial X-ray absorption within the insertions and a high spatial resolution. The size of the cross-section of the insertion is also determined by the material of the insertion. In general the spacing between the insertions will be in the range of 5 mm–20 mm. Due to the fact that the dimensions of the insertions as well as the spacing between them are a-priori known, one can overrule the potentiometer read-out of the tabletop position if an insertion is detected in a reconstructed image.

A further embodiment of the CT-apparatus according to the invention is characterized in that the insertions have a substantially rectangular cross-section. To calibrate the position of the tabletop one uses the known coordinate of, for example, the geometrical center of an insertion. However, it is also possible to use the edge to perform the coordinate calibration. In general, one can use insertions, which have a circular cross-section, however the advantage of using insertions with the rectangular cross-section is the convenience with which the edge detection algorithms can be fulfilled.

A further embodiment of the CT-apparatus according to the invention is characterized in that every insertion has a higher X-ray attenuation coefficient than the material of the tabletop. This embodiment ensures the optimal contrast between the insertions and the material of the tabletop, the latter being often fabricated from elements with low Z-value. Having insertions which have higher X-ray attenuation coefficient leaves the manufacturer a broader material choice. For example, Al is a material which can be used for manufacturing of these insertions.

A further embodiment of the CT-apparatus according to the invention is characterized in that detection means is provided to perform a detection of the position of any insertion on the X-ray transmission image. The insertion detection is performed on the lateral projection image, based on the insight that this projection provides the highest X-ray attenuation within the insertions and does not distort the geometry of the projection of the insertion. As an example of said detection one can mention well-known edge detection algorithms in case one calibrates the tabletop coordinate on the edge of the insertion, or edge detection algorithms in combination with Full Width of Half Maximum determination algorithms, if one calibrates the tabletop coordinate on the geometrical center of the insertion.

A further embodiment of the CT-apparatus according to the invention is characterized by first calibration means, which are provided to perform a calibration of the position of the tabletop in the first longitudinal direction. In this embodiment in order to acquire an optimum image of the marker the control means are available to perform a number of X-ray acquisitions per one degree of the X-ray source rotation. Further, the usage is made of, for example, a Least Square Fit algorithm to establish with a certain degree of confidence the spatial position of the insertion. Next, the calibration means overrule the read-out of the potentiometers in case an insertion is detected on the reconstructed image. If such correction is needed, the prescription means prescribe the coordinate of the insertion as the true coordinate of this reconstructed image.

A further embodiment of the CT-apparatus according to the invention is characterized by second calibration means, which are provided to perform a calibration of the position of the tabletop in the direction, substantially orthogonal to both the first and the second longitudinal directions. It is known from the clinical practice that in some cases the tabletop can bend substantially in some operational conditions. As has been explained earlier,

DETAILED DESCIPTION OF THE INVENTION it is necessary to know the spatial position of the image plane with high accuracy. The second calibration means perform the calibration of the tabletop in a second direction, which often will coincide with the vertical direction. If a part of the tabletop is moved out of its original horizontal plane, the position of the insertion on the lateral transmission image will be lower than the expected one. By measuring the value of this displacement, one can correct for the tabletop movements out of its original plane.

The further embodiment of the CT-apparatus according to the invention is characterized by third calibration means, which are provided to perform a calibration of a tilt angle of the tabletop with respect to the plane of the transmission image. Due to the current medical practice it is required that the longitudinal axis of the tabletop is perpendicular to the plane of the X-ray source rotation. Small angle misalignments cause inaccuracies in the resulting image reconstruction. To detect and/or to correct for these small-angle misalignments the third calibration means perform the detection of the absolute dimensions of the cross-section of the insertions. If the tabletop is misaligned with the first longitudinal direction, the projection of insertions in the lateral direction will be distorted, resulting in a slightly enlarged image of an original geometric figure of a cross-section of the insertion with deteriorated edge sharpness. The third calibration means according to the invention can comprise a well-known algorithm for a Full Width of Half Maximum determination, in case one performs the misalignment detection by calculating the absolute dimensions of the cross-section of insertions. Alternatively, one can use an edge detection algorithm if one performs the misalignment detection by calculating the sharpness of the edge of the insertion.

These and other aspects of the invention will be discussed using the figures, where the corresponding numerals represent corresponding parts of the construction, wherein

BRIEF DESCRIPTION OF THE DRAWING FIGURES

FIG. 1 presents a schematic view of the X-ray exposure geometry for a helical CT acquisition mode.

FIG. 2 presents a schematic view of the detection means to perform a detection of the position of the tabletop in the first longitudinal direction, FIG. 3 presents a schematic view of the detection means to perform a detection of the position of the tabletop in the vertical direction, FIG. 4 presents a schematic view of the detection means to perform a calibration of a tilt angle of the tabletop with respect to the vertical plane.

FIG. 1a presents a schematic view of the X-ray exposure geometry for a helical CT acquisition mode. The patient is positioned on the patient support tabletop 1, which table is then moved into a CT gantry (not shown) of the CT apparatus. In the CT apparatus the patient is exposed with a beam of the X-ray radiation 2 from the X-ray source 3. The X-ray source 3 can be rotated in the plane of the CT gantry to produce X-ray transmission images 20 from different exposure directions. It is possible to expose the patient in two modes: step and shoot mode and a helical acquisition mode. For the latter, the patient support tabletop 1 is continuously transported in its longitudinal direction during the rotation of the X-ray source 3. The schematic line 5 represents the movement of the X-ray source 3 with respect to the patient support tabletop 1, direction z representing the first longitudinal direction. After the acquired transmission images 20 are reconstructed (see FIG. 1b), one obtains a set of diagnostic images 30 (FIG. 1c). The information about a spatial position of a single reconstructed image is obtained from the controls of the transport of the patient tabletop. In general, since the patient table has to be moved in the first longitudinal direction z during the acquisition, the precision of the tabletop position determination has to be higher that the voxel size. The helical acquisition mode is much more sensitive to positioning errors than the conventional (step and shoot) scans. Every positioning error will result in redundant or incomplete data capture with subsequent reconstruction artefacts. However, if the positioning error is not too large and a true position is known, the reconstruction can resolve this problem and correct for it, yielding better image quality. It is, therefore, advantageous to know the true positions of the patient tabletop 1.

Figure 1D:
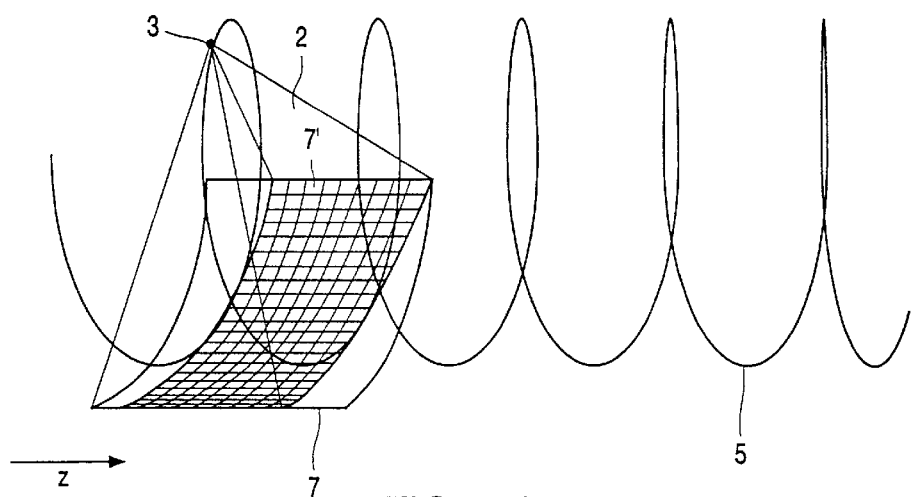
Figure 2A:
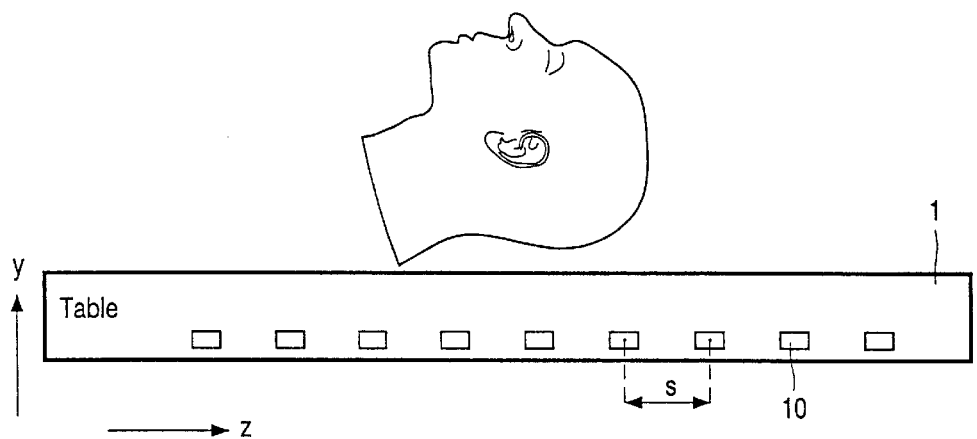
Figure 2B:
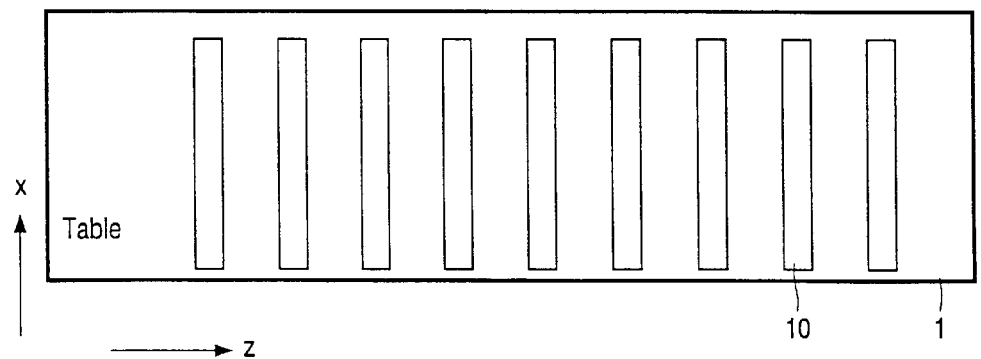
Figure 2C:
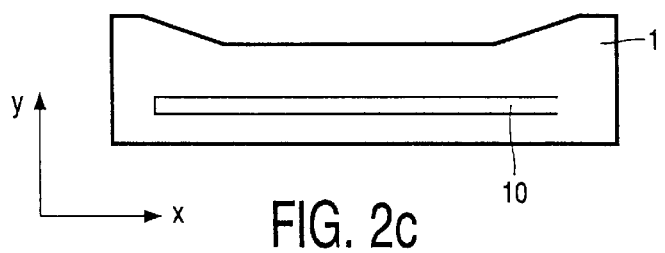
Figure 2D:
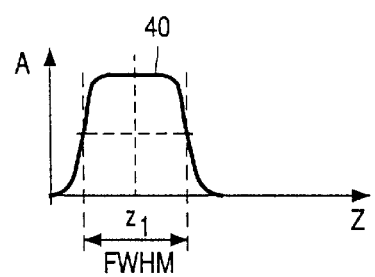

FIG. 1d presents a schematic representation of the spatial trajectory of the X-ray source 3 relative to the patient support tabletop 1. For a cone beam CT, one uses a two-dimensional detector array 7 to detect the X-ray transmission in every detector element 7' from the patient, which is exposed to the cone beam 2. The characteristic size of such a detector 7 is in the order of 2 cm. For clarity reasons the patient is not depicted in FIG. 1d. The arrow z represents the first longitudinal direction, coinciding with one direction of the transport of the tabletop 1. Due to the cone-beam 2, the image reconstruction algorithm will use the information from all detector elements in the z-direction. Due to the fact that the dimensions of every detector element 7' are known, the minimal resolution in the z-direction equals the size of detector elements 7' in this direction. However, the mechanics for the transport of the tabletop 1 have tolerances which are larger that the size of the detector element 7'. To improve the accuracy of the position determination of the tabletop 1, one uses the extra calibration means, which are explained below.

FIG. 2 presents a schematic view of the detection means to perform a detection of the position of the tabletop 1 in the first longitudinal direction z. The detection means according to the invention comprise the insertions 10 of a contrast material, relative to the material of the tabletop 1. For better contrast, it might be advantageous to use a material for the insertions 10 with a high Z number, as tabletops 1 are often manufactured from materials with low Z number. Aluminium is an example of a suitable material for insertions, as it is not heavy and has good X-ray absorption properties in the X-ray energy range used in the CT technology. In general, the absolute dimensions of the insertions 10 will be determined by the required spacing between the insertions in the z-direction and by X-ray absorption properties of the material of the insertions. FIGS. 2a, b and c present the three cross sections of the tabletop 1 in order to illustrate the geometry of these insertions 10. In the given example the insertions 10 have a rectangular cross-section, however the scope of the invention is not limited to it. Using these insertions 10 one can detect or correct for the inaccuracies in the position of the tabletop 1 in the first longitudinal direction z. According to the invention the insertions 10 are arranged within the tabletop substantially in one xz-plane, parallel to each other and perpendicular to the first longitudinal direction z with their longest dimension, defined as the second longitudinal direction. Therefore, the maximum absorption direction for the X-ray beam will coincide with the direction x, as shown in FIG. 2b. During the helical acquisition mode the tabletop 1 is continuously transported in the z direction. The corresponding tabletop position determination means, for example potentiometers, provide the information about this position. However, the tolerance of these tabletop position determination means is in the order of 2 mm, which might not be sufficient for the accuracy requirement of the image reconstruction algorithm. Therefore, one can use a detection of one of the insertions as a fine-tuning of the tabletop position determination. This idea is based on the fact that the spatial position as well as dimensions of each insertion are a-priori known and are provided to the image reconstruction algorithm. When the tabletop is transported in the z-direction the X-ray projection in the x-direction across an insertion 10 is given by FIG. 2d, see graph 40, where absorption A within an insertion 10 is plotted against the tabletop displacement z. Using a well-known algorithm to perform a quantitative analysis of the graph 40, for example, to determine the center of the graph 40, one can prescribe the true coordinate z1 to the resulting reconstructed image. For an accurate performance of this tabletop position determination it is required that the spacing s between the consecutive insertions will be smaller that the dimension of the X-ray detector in the first longitudinal direction, both dimensions being calculated for the same X-ray projection plane. According to the invention the calibration means to perform a calibration of the tabletop position in the first longitudinal direction comprise the set of insertions 10, as well as dedicated software and hardware to perform this calibration.

Figure 3A:
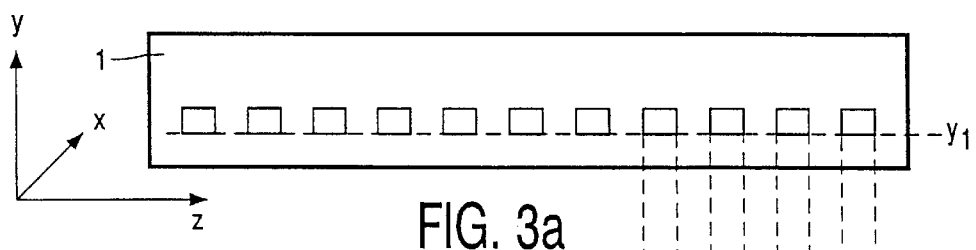
Figure 3B:
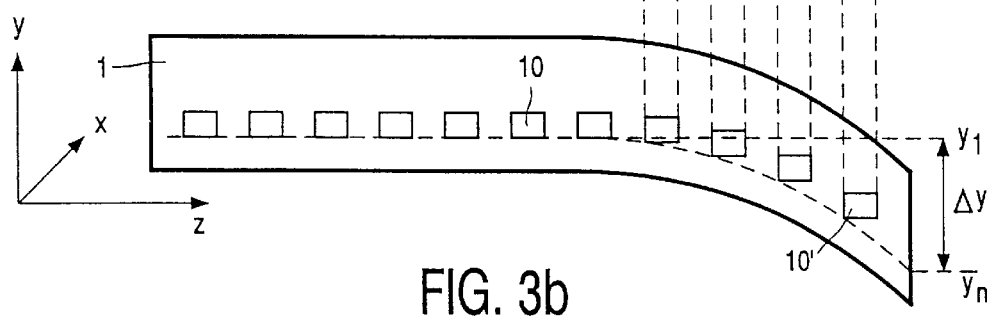
Figure 3C:
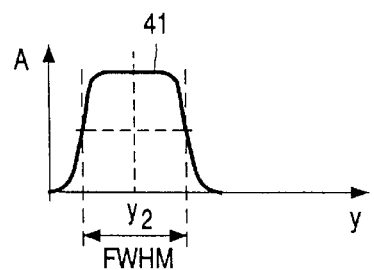

FIG. 3 presents a schematic view of the detection means to perform a detection of the position of the tabletop 1 in the vertical direction. The detection algorithm uses the X-ray projections in the x-direction, where the cross-sections of the insertions 10 are visible. FIG. 3a presents a schematic representation of the tabletop 1 in a non-loaded condition. The dimensions of the insertions 10 are known, as well as their spatial position at least in the z- and in the y-directions. It might be advantageous to arrange the insertions substantially in one plane y1. When a patient is positioned on the tabletop 1, it is possible that the position of the tabletop in the y-direction changes, as shown in FIG. 3b. The insertions 10 are no longer in one plane y1, but exhibit an individual displacement Δy, which is illustrated schematically for the insertion 10'. In order to improve the accuracy of the insertion detection on the X-ray projections, a number of X-ray acquisitions per 1° of the X-ray source rotation can be taken in the x-direction. The detection means to perform a detection of the local position of the tabletop 1 in the vertical direction y comprise also a computer algorithm to perform an analysis of the absorption pattern within an insertion along the y-direction. An example of such an absorption graph 41 is given in FIG. 3c, where the absorption A across an insertion 10' as function of a vertical displacement y is presented. The computing algorithm can comprise the means to determine the Full Width of the Half Maximum of such a graph and using this information an actual displacement y2 can be determined. The resulting coordinate of the projection plane will be used as input for the calibration means which prescribe the correct spatial position form the reconstructed image.

Figure 4A:
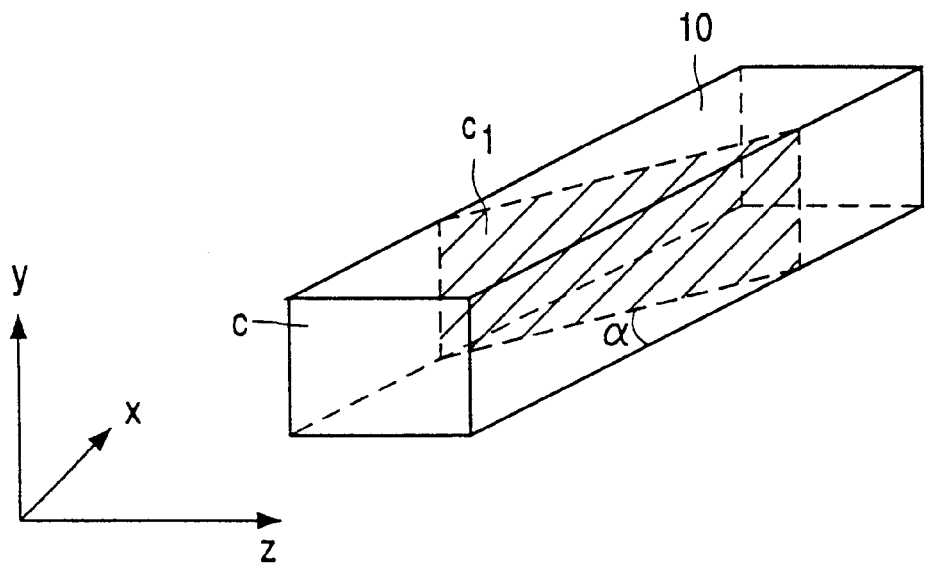
Figure 4B:
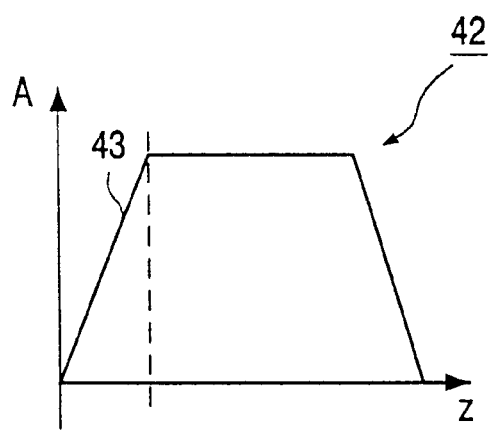

FIG. 4 presents a schematic view of the detection means to perform a calibration of a tilt angle of the tabletop with respect to the vertical plane. In CT acquisition it is required that the tabletop is perpendicular to the rotation plane of the X-ray source of the CT apparatus. However, it is possible that the tabletop 1 has some misalignment α, which can result in the inaccurate image reconstruction. It is possible to use the insertions 10 to detect the tabletop misalignment α and to correct for this misalignment during the image reconstruction. FIG. 4a shows a single insertion 10, the tabletop and the X-ray source are not shown for the sake of clarity. When no misalignment is present the resulting cross-section of the insertion of the X-ray projection in x-direction is given by c, the dimensions of this cross-section being a-priori known. In case the tabletop and, thus the insertions are misaligned for an angle Δ, one will obtain the cross-section of the insertion 10 on the X-ray projection as given by c1. FIG. 4b shows the corresponding curve 42 of the X-ray absorption A across the insertion as function of the displacement along the first longitudinal direction z. The slope of the rising part 43 of the curve 42 is a measure of the tabletop misalignment a. The calibration means comprise an algorithm to perform a quantitative analysis of, for example, the slope 43 of this curve, the resulting number representing the actual misalignment. The image reconstruction algorithm uses this number to correct the reconstruction coordinates form this misalignment.

What is claimed is:

1. A CT-apparatus comprising an investigation bore with an X-ray source (3) and an X-ray detector (7) to generate an X-ray transmission image (20) of an object to be investigated, a table with an elongated tabletop (1) with a first longitudinal direction (z) to support the object, which tabletop (1) is translatable into the investigation bore in its first longitudinal direction (z), which tabletop (1) comprises elongated mutually parallel insertions (10) of a contrast material relative to the material of the tabletop (1) for calibration purposes, said contrast material having a different X-ray attenuation coefficient than the material of the tabletop, said insertions (10) having a second longitudinal direction (x), characterized in that the insertions (10) are arranged with the second longitudinal direction (x) orthogonally to the first longitudinal direction (z), wherein the spacing (s) between the insertions (10) in the first longitudinal direction (z) is smaller than a dimension of the X-ray detector (7) in the first longitudinal direction (z).

2. A CT-apparatus as claimed in claim 1, wherein the insertions (10) have a substantially rectangular cross-section (c).

3. A CT-apparatus as claimed in claim 1, wherein every insertion (10) has a higher X-ray attenuation coefficient than the material of the tabletop (1).

4. A CT-apparatus as claimed in claim 1, wherein detection means are provided to perform a detection of the position of any insertion (10) on the X-ray transmission image (20).

5. A CT-apparatus as claimed in claim 4, wherein first calibration means are provided to perform a calibration of the position of the tabletop (1) in the first longitudinal direction (z).

6. A CT-apparatus as claimed in claim 4, wherein second calibration means are provided to perform a calibration of the position of the tabletop (1) in the direction (y), substantially orthogonal to both the first (z) and the second (x) longitudinal directions.

7. A CT-apparatus as claimed in claim 4, wherein third calibration means are provided to perform a calibration of a tilt angle ($\alpha$) of the tabletop (1) with respect to the plane of the transmission image.

* * * * *